United States Patent

Law et al.

Patent Number: 5,077,160
Date of Patent: Dec. 31, 1991

[54] PHOTOCONDUCTIVE IMAGING MEMBERS WITH FLUORINATED SQUARAINE COMPOSITIONS

[75] Inventors: Kock-Yee Law, Penfield; F. Courtney Bailey, Webster, both of N.Y.

[73] Assignee: Xerox Corporation, Stamford, Conn.

[21] Appl. No.: 524,947

[22] Filed: May 18, 1990

[51] Int. Cl.$^5$ .................................... G03G 5/06
[52] U.S. Cl. ........................ 430/59; 430/60; 430/65; 430/73; 564/307
[58] Field of Search ............... 430/59, 60, 65, 73, 564/307

[56] References Cited

U.S. PATENT DOCUMENTS

| | | | |
|---|---|---|---|
| 4,521,621 | 6/1985 | Yanus et al. | 564/307 |
| 4,607,124 | 8/1986 | Kazmaier et al. | 564/307 |
| 4,746,756 | 5/1988 | Kazmaier et al. | 564/307 |
| 4,886,722 | 12/1989 | Law et al. | 430/59 |

FOREIGN PATENT DOCUMENTS 0172321 2/1986 European Pat. Off. .

Primary Examiner—Marion E. McCamish
Assistant Examiner—S. Rosasco
Attorney, Agent, or Firm—E. O. Palazzo

[57] ABSTRACT

The fluorinated squaraines

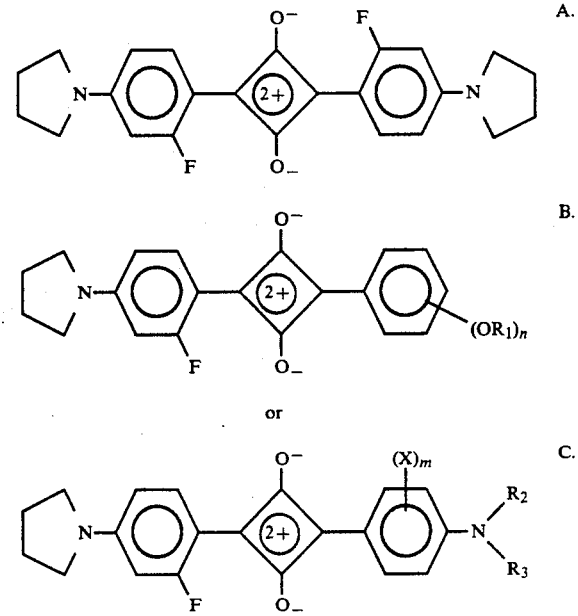

wherein $R_1$, $R_2$ and $R_3$ are independently selected from alkyl or aryl; X is hydrogen, hydroxy, alkyl, alkoxy or halogen; n is a number of 1 to about 3; and m is a number of from 0 to 2; and imaging members thereof.

50 Claims, 4 Drawing Sheets

+  →

+  →

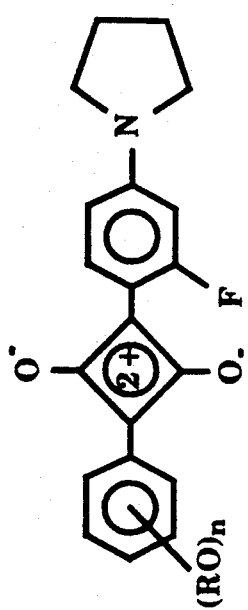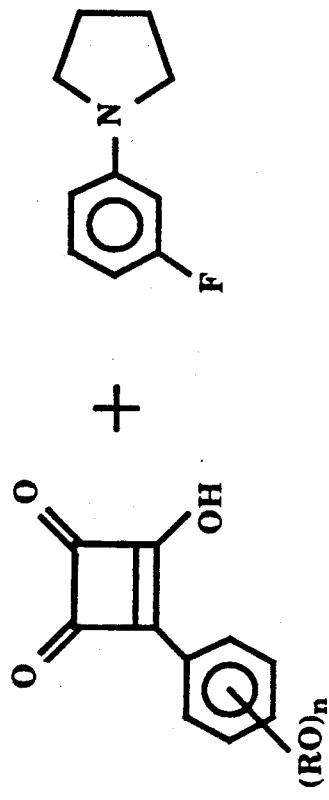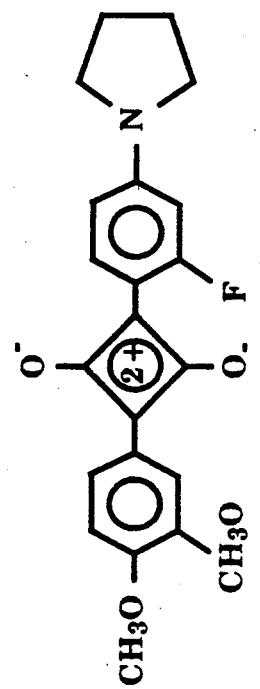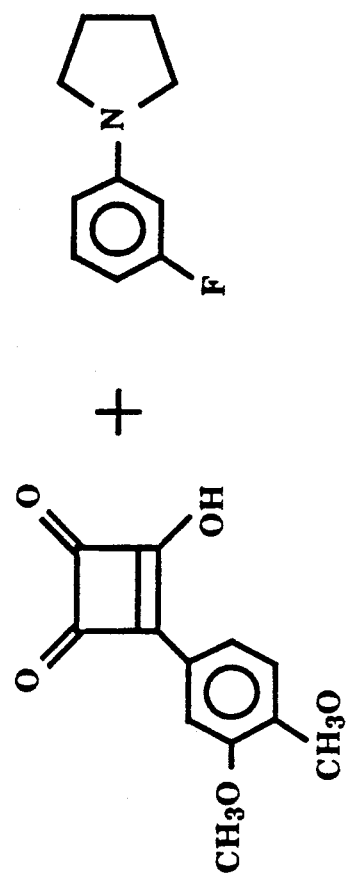
FIG. 3
FIG. 4

PHOTOCONDUCTIVE IMAGING MEMBERS WITH FLUORINATED SQUARAINE COMPOSITIONS

BACKGROUND OF THE INVENTION

This invention is generally directed to squaraine compounds or compositions, and to processes for the preparation thereof. More specifically, the present invention is directed to symmetrical and unsymmetrical fluorinated squaraine compositions prepared, for example, from N-pyrrolidino fluoroanilines. In one embodiment of the present invention, there are provided fluorinated squaraine compositions with excellent xerographic properties, inclusive of high charge acceptance, low dark decay, high photosensitivity, and improved cyclic stability when these compositions are incorporated into photoconductive imaging members. In another embodiment of the invention of the present application there are provided imaging members with photoconductive layers comprised of the fluorinated squaraines illustrated herein, and charge or hole transport layers, especially those comprised of aryl amines, which members are sensitive to light in the wavelength region of from about 400 to about 1,000 nanometers. Therefore, the resulting members are responsive to visible light, and especially infrared illumination originating from laser printing apparatuses wherein, for example, gallium arsenide diode lasers are selected. The photoresponsive imaging members of the present invention can also, for example, comprise, situated between a photogenerating layer and a hole transporting layer, or situated between a photogenerating layer and a supporting substrate with a charge transport layer in contact with the photogenerating layer, a photoconductive composition comprised of the fluorinated squaraines illustrated herein. Advantages associated with the process of the present invention include the selection of the N-pyrrolidone-3-fluoroaniline as a reactant thereby enabling, for example, high yields of products as compared, for example, to fluorinated squaraine products synthesized from N,N-dimethyl-3-fluoroaniline; and moreover, the resulting products as result of the reactant selected are nontoxic, substantially nontoxic or nonmutagenic in an embodiment of the present invention.

Numerous different xerographic photoconductive members, including members with photogenerating pigments of squaraines and processes thereof, are known. There are also known photoreceptor materials comprised of inorganic or organic materials wherein the charge carrier generating, and the charge carrier transport functions are accomplished by discrete contiguous layers. Additionally, layered photoreceptor materials are disclosed in the prior art, which include an overcoating layer of an electrically insulating polymeric material. Further, there are disclosed in the prior art layered photoresponsive devices including those comprised of separate generating layers, and transport layers as described in U.S. Pat. No. 4,265,990, the disclosure of which if totally incorporated herein by reference; and overcoated photoresponsive materials containing a hole injecting layer, overcoated with a hole transport layer, followed by an overcoating of a photogenerating layer; and a top coating of an insulating organic resin, reference U.S. Pat. No. 4,251,612. Examples of photogenerating layers disclosed in these patents include trigonal selenium and phthalocyanines, while examples of transport layers include certain diamines as mentioned therein. Also, there is illustrated in U.S. Pat. No. 4,415,639, the disclosure of which is totally incorporated herein by reference, the use of squaraine compositions, such as hydroxy squaraines, as a photoconductive layer in an infrared sensitive photoresponsive device. More specifically, there is described in this patent an improved photoresponsive device containing a substrate, a hole blocking layer, an optional adhesive interfacial layer, an inorganic photogenerating layer, a photoconductive composition capable of enhancing or reducing the intrinsic properties of the photogenerating layer, which photoconductive composition is selected from various squaraine compositions, including hydroxy squaraine compositions, and a hole transport layer. Other patents disclosing photoconductive devices with squaraines are U.S. Pat. Nos. 4,471,041; 4,486,520; 4,508,803; 4,507,480; 4,552,822; 4,390,610; 4,353,971; 4,391,888; 4,607,124 and 4,746,756. In the '124 patent, the disclosure of which is totally incorporated herein by reference, there are illustrated processes for the preparation of a squaraine mixture, one of which may be a fluorinated component, see column 5, wherein the known squaric acid reaction is accomplished in the presence of a fluoroaniline, and the use thereof in photoconductive imaging members. The '756 patent, the disclosure of which is totally incorporated herein by reference, illustrates layered imaging members with certain fluorinated squaraines, wherein $R_2$ and $R_3$ may be a heterocyclic, such as 2-pyrolyl, see columns 3, 4, 5 and 6, for example.

Furthermore, there are illustrated in U.S. Pat. No. 4,624,904, the disclosure of which is totally incorporated herein by reference, photoconductive imaging members with unsymmetrical hydroxy squaraine compositions, and aryl amine hole transport layers. The aforementioned unsymmetrical squaraine compounds can be prepared, for example, by the initial preparation of an aryl cyclobutenedione intermediate, followed by the reaction thereof with a substituted aniline. More specifically, with respect to method A illustrated in the '904 patent, the aryl cyclobutenedione is prepared by heating with reflux at a temperature of from about 40° to about 50° C., depending on the solvent selected; about 20 millimoles to about 50 millimoles of substituted aniline; from about 60 millimoles to about 150 millimoles of dihalocyclobutenedione; and from about 100 milliliters to about 1,000 milliliters of a Federal Craft solvent inclusive of, for example, carbon disulfide nitrobenzene or methylene chloride. This reaction is accomplished in the presence of from about 200 to about 900 millimoles of a catalyst, such as aluminum chloride, and the resulting substituted aniline is reacted with a hydroxy substituted aniline in the presence of an aliphatic alcoholic solvent. Subsequent to separation, there are obtained the desired unsymmetrical squaraine compounds. Also, in U.S. Pat. No. 4,521,621, there are described photoresponsive imaging members containing unsymmetrical squaraines, reference for example the formula in column 7, line 60, by forming a mixture of squaric acid, a primary alcohol, a first tertiary amine, and a second tertiary amine.

In U.S. Pat. No. 4,524,220, the disclosure of which is totally incorporated herein by reference, there is illustrated a squaraine process by the reaction of squaric acid and an aromatic aniline in the presence of an aliphatic amine. Also, in U.S. Pat. No. 4,524,219 there is described a process for the preparation of squaraines by the reaction of an alkyl squarate, and an aniline in the presence of an aliphatic alcohol, and an optional acid catalyst. Moreover, disclosed in U.S. Pat. No. 4,524,218 are processes for the preparation of squaraines by the reaction of squaric acid with an aromatic amine, and a composition selected from the group consisting of phenols, and phenol squaraines, which reaction is accomplished in the presence of an aliphatic alcohol, and an optional azeotropic catalyst. Other processes for preparing squaraines are illustrated in U.S. Pat. No. 4,525,592, wherein there is described the reaction of a dialkyl squarate, and an aniline in the presence of an aliphatic alcohol and an acid catalyst; and U.S. Pat. No. 4,746,756 mentioned herein wherein the fluorinated squaraines disclosed are prepared by the reaction of an aromatic fluorinated amine and squaric acid in the presence of an aliphatic alcohol and an optional azeotropic cosolvent.

In U.S. Pat. No. 4,886,722, the disclosure of which is totally incorporated herein by reference, there is illustrated the provision of certain unsymmetrical squaraine compositions, and processes for the preparation thereof. More specifically, there are disclosed in the '722 patent photoconductive imaging members containing as photoconductive compositions unsymmetrical squaraines of the following formula

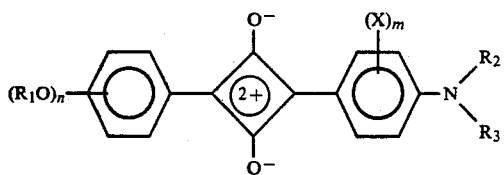

wherein $R_1$, $R_2$ and $R_3$ are independently selected from alkyl groups or aryl groups; X is hydroxy, hydrogen, alkyl, alkoxy, or halo; n is a number of from 1 to about 3; and m is a number of from 0 to about 2. Preferred halogens include fluorine and chlorine. Examples of alkyl groups include those containing from about 1 to about 25 carbon atoms such as methyl, ethyl, propyl, butyl, pentyl, hexyl, heptyl, dodecyl and the like; while examples of aryl groups include those with from about 6 to about 24 carbon atoms including substituted aryl groups such as phenyl and benzyl. Alkoxy groups are represented by those containing from about 1 to about 10 carbon atoms such as methoxy, propoxy, butoxy, pentoxy, heptoxy, and the like, inclusive in some situations of aryl alkoxy substituents such as phenyl alkoxy. Halo includes fluoride, bromide, chloride and iodide.

Specific examples of unsymmetrical squaraines illustrated in the '722 patent include 4-dimethylaminophenyl-4'-methoxyphenyl squaraine; 2-hydroxy-4-dimethylaminophenyl-4'-methoxyphenyl squaraine; 2-methyl-4-dimethylaminophenyl-4'-methoxyphenyl squaraine; 2-fluoro-4-dimethylaminophenyl-4'-methoxyphenyl squaraine; 2-methoxy-4-dimethylaminophenyl-4'-methoxyphenyl squaraine; 4-benzylmethylaminophenyl-4'-methoxyphenyl squaraine; 4-dimethylaminophenyl-3',4'-dimethoxyphenyl squaraine; 2-hydroxy-4-dimethylaminophenyl-3',4'-dimethoxyphenyl squaraine; 2-methyl-4-dimethylaminophenyl-3',4'-dimethoxyphenyl squaraine; 2-fluoro-4-dimethylaminophenyl-3',4'-dimethoxyphenyl squaraine; 2-methoxy-4-dimethylaminophenyl-3',4'-dimethoxyphenyl squaraine; 4-dimethylaminophenyl-3',4',5'-trimethoxyphenyl squaraine; 2-hydroxy-4-dimethylaminophenyl-3',4',5'-trimethoxyphenyl squaraine; 2-chloro-4-dimethylaminophenyl-4'-methoxyphenyl squaraine; 2-chloro-4-dimethylaminophenyl-3',4'-dimethoxyphenyl squaraine; 4-diethylaminophenyl-4'-methoxyphenyl squaraine; and 4-diethylaminophenyl-3',4'-dimethoxyphenyl squaraine.

The squaraine compositions of the '722 patent are generally prepared by a cycloaddition-condensation reaction. More specifically, these squaraines can be prepared by condensing, for example, a 1-alkoxyaryl-2-hydroxycyclobutene-3,4-dione derivative with an N,N-dialkylaniline derivative, such as 1-3',4'-dimethoxy-phenyl-2-hydroxycyclobutene-3,4-dione or 3-fluoro-N,N-dimethylaniline in a molar ratio of about 1 to 6, and preferably in a ratio of about 1 to 3 in the presence of an aliphatic alcohol, such as propanol, and an optional drying reagent. About 500 milliliters of alcohol per 0.1 mole of 1-alkoxyaryl-2-hydroxycyclobutene-3,4-dione are selected, however, up to about 1,000 milliliters of alcohol to about 0.5 to 1 mole of 1-alkoxyaryl-2-hydroxycyclobutene-3,4-dione can be selected. The drying reagent can be heterogeneous such as molecular sieves or homogeneous such as a trialkyl orthoformate. A ratio of 1 to 10 equivalents of drying reagent, more specifically tributyl orthoformate, can be used with a ratio of about 1 to 4 to the cyclobutene dione being preferred. Also, the reaction is generally accomplished at a temperature of about 60° C. to about 130° C., and preferably at a temperature of 70° C. to about 100° C. with stirring until the reaction is completed. Subsequently, the desired product can be isolated from the reaction mixture by known techniques such as filtration, and the product is identified by analytical tools including IR, NMR, and mass spectrometry. Further, carbon, hydrogen, fluorine, nitrogen and oxygen elemental analysis can be selected for aiding the identification of the product.

The 1-alkoxyaryl-2-hydroxycyclobutene-3,4-dione reactant can be prepared as indicated in the literature, and specifically by a known [2+2] cycloaddition process involving a tetraalkoxy olefin and an alkoxyarylketene generated in situ by the reaction of an alkoxyarylacetyl chloride and a base. Thus, for example, 3,4-dimethoxyphenylacetyl chloride can be reacted with tetraethoxyethylene in n-hexane in the presence of triethylamine. The ratio of acid chloride to tetraethoxyethylene is about 1 to 10 with 1 to 4 being preferred. The amount of triethylamine used will vary, however, usually an amount equivalent to the amount of the acid chloride is selected, and the reaction mixture is stirred at room temperature until the reaction is complete. Also, the [2+2] cyclo adduct product mixture can be hydrolyzed directly by refluxing in an aqueous hydrochloric acid solution or pre-purified by stirring with silica gel or alumina in a solvent, such as n-hexane or ether, before the hydrolysis. The hydrolyzed product is then purified by conventional technique such as recrystallization. This results in reactants such as 1-4'-methoxyphenyl-2-hydroxycyclobutene-3,4-dione, 1-3',4'-dimethoxyphenyl-2-hydroxycyclobutene-3,4-dione, and 1-3',4',5'-trimethoxyphenyl-2-hydroxycyclobutene-3,4-dione, which can then be reacted with a N,N-dialkylaniline enabling the formation of the unsymmetrical squaraines.

The squaraines of the aforementioned '722 patent can be incorporated into various photoconductive imaging members. One such member is comprised of a supporting substrate, a hole transport layer and as a photoconductive layer situated between the supporting substrate, and the hole transport layer the squaraines. In another embodiment of the copending application, there is envisioned a layered photoresponsive device comprised of a supporting substrate, a certain squaraine photoconductive layer and situated between the supporting substrate and the photoconductive layer, a hole transport layer. In one specific illustrative embodiment of the copending application, the photoresponsive device can be comprised of (1) a supporting substrate, (2) a hole blocking layer, (3) an optional adhesive interface layer, (4) an unsymmetrical squaraine photogenerating layer, and (5) a hole transport layer. Thus, a specific photoresponsive device of the copending application can be comprised of a conductive supporting substrate, a hole blocking metal oxide layer in contact therewith, an adhesive layer, an unsymmetrical squaraine photogenerating material overcoated on the optional adhesive layer, and as a top layer, a hole transport layer comprised of certain diamines dispersed in a resinous matrix. The photoconductive layer composition, when in contact with the hole transport layer, is capable of allowing holes generated by the photogenerating layer to be transported. Examples of aryl amine hole transport molecules that may be selected for the photoconductor devices are illustrated in U.S. Pat. No. 4,265,990, the disclosure of which is totally incorporated herein by reference.

The photoresponsive devices described in the '722 patent and the imaging members of the present invention can be utilized in various imaging systems including xerographic imaging processes. Additionally, the imaging members of the present invention can be selected for imaging and printing systems with visible light and/or infrared light. In this embodiment, the photoresponsive devices may be negatively charged, exposed to light in a wavelength of from about 400 to about 850 nanometers, either sequentially or simultaneously, followed by developing the resulting image and transferring to paper. The above sequence may be repeated many times.

There were reported in a patentability search letter U.S. Pat. Nos. 4,521,621; 4,607,124 and 4,746,756, mentioned hereinbefore, of which the '756 patent illustrates fluorinated squaraines wherein $R_1$, $R_2$ and $R_3$ may be a heterocyclic, see column 5, lines 4 to 29, for example. Further, in *Angew Chem. Int. Ed. Engl S*, 894 (1966), H. E. Spenger and W. Ziegenbein there is illustrated the preparation of squaraines by condensing one equivalent of squaric acid and two equivalents of aniline derivatives under azeotropic conditions; many squaraines have been prepared by the aforementioned processes, reference for example U.S. Pat. Nos. 3,617,270; 3,824,099; 4,175,956; 4,486,520 and 4,508,803; and hydroxy and certain fluorinated squaraines for xerographic photoreceptor applications, reference K. Y. Law and F. C. Bailey, *J. Imaging Science*, 31, 172 (1987).

Although the above squaraines, and processes thereof are suitable for their intended purposes, there continues to be a need for other photoconductive squaraines. Additionally, and more specifically there remains a need for simple, economical processes for preparing certain fluorinated squaraine compositions with stable properties, which when incorporated into photoconductive devices result in reduced dark decay characteristics, and increased charge acceptance values as compared to many similar squaraine compositions. In addition, there remains a need for photoconductive imaging members with certain stable electrical characteristics, that is for example the aforementioned imaging members are electrically stable for over 100,000 xerographic imaging cycles in embodiments thereof. In addition, imaging members with the aforementioned fluorinated, including unsymmetrical and symmetrical, squaraines of the present invention in embodiments thereof are sensitive to a broad range of wavelengths, including visible and infrared light, such as of from about 400 to about 850 nanometers, enabling such members to be useful in electrophotographic imaging and printing processes, including processes wherein diode lasers are selected.

SUMMARY OF THE INVENTION

It is therefore an object of the present invention to provide certain squaraine compositions and processes for the preparation thereof, and more specifically aniline derivatives of N-pyrrolidino-m-fluoroaniline (PFA), and the squaraines thereof.

Another object of the present invention is to provide certain fluorinated squaraine compositions, both unsymmetrical and symmtrical, and imaging members comprised of these squaraines, which members are sensitive to wavelengths of from about 400 to about 1,000 and preferably from about 400 to about 850 nanometers.

In another object of the present invention there are provided improved processes for preparing fluorinated squaraine compositions from N-pyrrolidinófluoroanilines, such as N-pyrrolidino-3-fluoroaniline, which when incorporated into photoresponsive imaging members possess excellent dark decay properties, high charge acceptance values, and electrical stability.

In yet another object of the present invention there are provided simple, economical processes for preparing fluorinated unsymmetrical squaraine compositions, which can be selected for layered photoconductive imaging members containing aryl amine hole transport layers.

A further object of the present invention resides in improved processes for obtaining symmetrical and unsymmetrical squaraine compositions of excellent sensitivity, and excellent cyclic stability when incorporated into layered imaging members with hole transport molecules.

Further, in another object of the present invention there are provided photoconductive imaging members with certain fluorinated unsymmetrical squaraines, which members are simultaneously responsive to infrared light, and to visible light.

Additionally, another object of the present invention resides in the provision of imaging and printing methods with the photoconductive imaging members described herein.

These and other objects of the present invention are accomplished by the provision of fluorinated squaraine compositions, and processes for the preparation thereof. More specifically, the present invention is directed to photoconductive imaging members with photoconductive fluorinated squaraine compositions represented by the following formulas

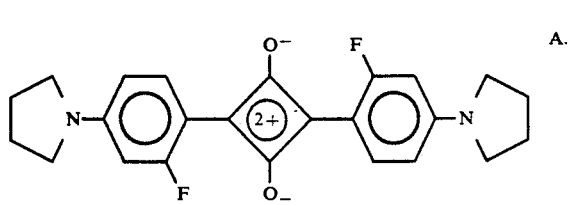

A.

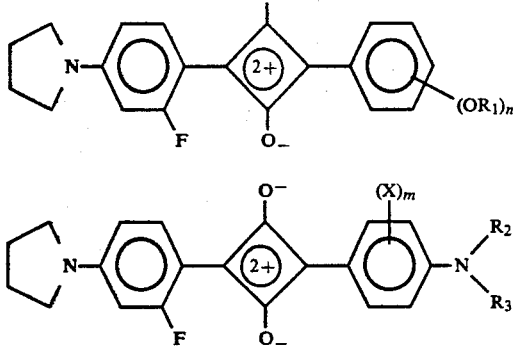

B.

C.

wherein $R_1$, $R_2$ and $R_3$ are independently selected from alkyl groups or aryl groups; X is hydrogen, hydroxy, alkyl, alkoxy or halo, n is a number of from 1 to 3; and m is a number of from 0 to 2. Preferred halogens include fluorine and chlorine.

Examples of alkyl groups include those containing from about 1 to about 25 carbon atoms such as methyl, ethyl, propyl, butyl, pentyl, hexyl, heptyl, octyl, nonyl, dodecyl and the like; while examples of aryl groups include those with from about 6 to about 24 carbon atoms including substituted aryl groups such as phenyl, naphthyl and benzyl. Alkoxy groups are represented by those containing from about 1 to about 10 carbon atoms such as methoxy, propoxy, butoxy, pentoxy, heptoxy, and the like, inclusive in some situations of aryl alkoxy substituents such as phenyl alkoxy. Halo includes fluoride, bromide, chloride and iodide.

Illustrative examples of specific squaraines of the present invention include bis(2-fluoro-4-N-pyrrolidinophenyl) squaraine; 2-fluoro-4-N-pyrrolidinophenyl-4'-dimethylaminophenyl squaraine; 2-fluoro-4-N-pyrrolidinophenyl-2'-hydroxy-4'-dimethylaminophenyl squaraine; 2-fluoro-4-N-pyrrolidinophenyl-2'-methyl-4'-dimethylaminophenyl squaraine; 2-fluoro-4-N-pyrrolidinophenyl-4'-dimethylaminophenyl squaraine; 2-fluoro-4-N-pyrrolidinophenyl-2'-fluoro-4'-dimethylaminophenyl squaraine; 2-fluoro-4-N-pyrrolidinophenyl-4'-methoxyphenyl squaraine; 2-fluoro-4-N-pyrrolidinophenyl-3',4'-dimethoxyphenyl squaraine; 2-fluoro-4-N-pyrrolidinophenyl-3',4',5'-trimethoxyphenyl squaraine; 2-fluoro-4-N-pyrrolidinophenyl-2'-methoxy-4'-dimethylaminophenyl squaraine; 2-fluoro-4-N-pyrrolidinophenyl-4'-methylbenzylaminophenyl squaraine; 2-fluoro-4-N-pyrrolidinophenyl-2'-chloro-4'-dimethylaminophenyl squaraine; 2-fluoro-4-N-pyrrolidinophenyl-9'-julolidinyl squaraine; 2-fluoro-4-N-pyrrolidinophenyl-8'-hydroxy-9'-julolidinyl squaraine; and 2-fluoro-4-N-pyrrolidinophenyl-8'-fluoro-9'-julolidinyl squaraine.

General and specific reaction schemes for obtaining the squaraines of the present invention are illustrated in FIGS. 1 through 6 wherein the substituents, such as R, X and n, are as defined herein.

In an embodiment of the present invention, reference the Reaction Schemes of FIGS. 1 and 2, the fluorinated squaraines can be prepared by the reaction of an N-pyrrolidone fluoroaniline, and squaric acid or an ester of squaric acid. More specifically, there is reacted N-pyrrolidino-3-fluoroaniline and squaric acid in a molar ratio of from about 4 to about 1, and preferably in a ratio of from about 2 to about 1, in the presence of an aliphatic alcohol, and an optional azeotropic cosolvent. About 400 milliliters of alcohol per 0.1 mole of squaric acid can be selected, however, up to 1,000 milliliters of alcohol to 0.1 mole of squaric acid can be selected. The reaction is generally accomplished at a temperature of from about 75° C. to about 150° C., and preferably at a temperature of 95° C. to 120° C. with stirring, until the reaction is completed. Subsequently, the desired product is isolated from the reaction mixture by known techniques such as filtration, and the product identified by analytical tools including NMR, and mass spectroscopy. Further, carbon, hydrogen, fluorine, nitrogen and oxygen elemental analysis is selected for aiding in identifying the resultant product.

The fluoroaniline reactant derivatives can be prepared by a number of processes thus, for example, known fluoroanilines, such as metafluoroaniline, can be reacted with 1,4-dibromobutane in a molar ratio of from about 1 to about 1.5 in the presence of a base such as soldium carbonate and a catalyst such as iodide in an alcoholic solvent such as 1-butanol. Generally, this reaction is accomplished by mixing the reactants and heating to a temperature of from 80° C. to about 200° C., preferably at about 118° C., followed by cooling and separation of the desired product by, for example, filtration. This results in the fluoroaniline reactant such as N-pyrrolidino-3-fluoroaniline.

In another embodiment of the present invention, reference for example the Reaction Schemes of FIGS. 3 and 4, the fluorinated squaraines can be prepared by the reaction of an N-pyrrolidone fluoroaniline, and 1-alkoxyaryl-2-hydroxycyclobutene-3,4-dione derivative in an alcoholic solvent in the presence of an optional drying reagent. More specifically, N-pyrrolidino-3-fluoroaniline and 1-3',4'-dimethoxyphenyl-2-hydroxycyclobutene-3,4-dione are reacted in a molar ratio of about 6 to 1 and preferably in a ratio of about 3 to 1 in the presence of an aliphatic alcohol, such as propanol, and an optional drying reagent. About 500 milliliters of alcohol per 0.1 moles of 1-alkoxyaryl-2-hydroxycyclobutene-3,4-dione are selected, however, up to about 1,000 milliliters of alcohol to about 0.5 to 1 mole of 1-alkoxyaryl-2-hydroxycyclobutene-3,4-dione can be selected. The drying reagent can be heterogeneous such as molecular sieves, or homogeneous such as trialkyl orthoformate. A ratio of 1 to 10 equivalents of drying reagent, such as tributyl orthoformate, can be used with a ratio of about 1 to 4 to the cyclobutene dione being preferred. Also, the reaction is generally accomplished at a temperature of about 60° C. to about 130° C., and preferably at a temperature of 70° C. to about 100° C. with stirring until the reaction is completed. Subsequently, the desired product can be isolated from the reaction mixture by known techniques such as filtration, and the product identified by analytical processes including IR, NMR, and mass spectrometry. Further, carbon, hydrogen, fluorine, nitrogen and oxygen elemental analysis can be selected for aiding the identification of the product.

The 1-alkoxyaryl-2-hydroxycyclobutene-3,4-dione reactant can be prepared as indicated in the literature, and specifically by a known [2+2] cycloaddition process involving a tetraalkoxy olefin and an alkoxyarylketene generated in situ by the reaction of an alkoxyarylacetyl chloride and a base. Thus, for example, 3,4-dimethoxyphenylacetyl chloride can be reacted with tetraethoxyethylene in n-hexane in the presence of triethylamine. The ratio of acid chloride to tetraethoxyethylene is about 1 to 10 with 1 to 4 being preferred. The amount of triethylamine used will vary, however, usually an amount equivalent to the amount of the acid chloride is selected and the reaction mixture is stirred at room temperature until the reaction is complete. Also, the [2+2] cyclo adduct product mixture can be hydrolyzed directly by refluxing in an aqueous hydrochloric acid solution or pre-purified by stirring with silica gel or alumina in a solvent such as n-hexane or ether, before the hydrolysis. The hydrolyzed product is then purified by conventional technique such as recrystallization. This results in reactants such as 1-4′-methoxyphenyl-2-hydroxycyclobutene-3,4-dione, 1-3′,4′-dimethoxyphenyl-2-hydroxycyclobutene-3,4-dione, 1-3′,4′,5′-trimethoxyphenyl-2-hydroxycyclobutene-3,4-dione, which can then be reacted with an N-pyrrolidone fluoroaniline as described herein enabling the formation of the fluorinated squaraines of the present invention in embodiments of the present invention.

In another embodiment of the present invention, reference the Reaction Schemes of FIGS. 5 and 6, the fluorinated squaraines can be prepared by the reaction of an N-pyrrolidino fluoroaniline and a 1-dialkylaminoaryl-2-hydroxycyclobutene-3,4-dione derivative in an alcoholic solvent in the presence of an optional drying reagent. More specifically, N-pyrrolidino-3-fluoroaniline and 1-p-dimethylaminophenyl-2-hydroxycyclobutene-3,4-dione in a molar ratio of about 6 to 1, and preferably in a ratio of about 3 to 1, were reacted in the presence of an aliphatic alcohol, such as ethanol butanol, methanol, propanol, and an optional drying reagent. Depending on the reactants selected and other factors, about 1 liter of alcohol per 0.1 mole of 1-dialkylaminoaryl-2-hydroxycyclobutene-3,4-dione is selected. However, up to 5 to 10 liters of alcohol per 0.1 to 0.5 mole of 1-dialkylaminoaryl-2-hydroxycyclobutene-3,4-dione can be selected. Optionally, the 1-dialkylaminoaryl-2-hydroxycyclobutene-3,4-dione may be introduced to the alcoholic reaction mixture (50/50) as a DMF (dimethylformamide), a DMSO (dimethylsulfoxide) solution, or as pure solid. The drying reagent can be heterogeneous, such as molecular sieves or homogeneous, such as a trialkyl orthoformate. A ratio of 1 to 10 equivalents of drying reagent, and more specifically tributyl orthoformate can be used with a ratio of about 1 to 4 to the cyclobutene dione being preferred. Also, the condensation reaction is generally accomplished at a temperature of from about 60° C. to about 130° C., and preferably at a temperature of 70° C. to about 100° C. with stirring until the reaction is completed. Subsequently, the desired squaraine product can be isolated from the mixture by known techniques such as filtration, and this product can be identified by analytical processes including IR and mass spectrometry. Further, carbon, hydrogen, and nitrogen elemental analysis can be selected for aiding the identification of the product.

The 1-p-dialkylaminoaryl-2-hydroxycyclobutene-3,4-dione or other dione reactant can be prepared by a reductive alkylation process. Specifically, 1-p-dialkylaminoaryl-2-hydroxycyclobutene-3,4-dione can be prepared by reducing the nitro cyclobutene dione with hydrogen in the presence of a catalyst, such as Palladium on carbon, and in the presence of an aldehyde. The temperature of the reductive alkylation process can, for example, be at about 20° C. to about 100° C. with 30° to 75° C. being preferred. The solvent for this aspect of the process can be DMF or DMSO or any solvent in which both the reactant and product are soluble. The concentration of Palladium that can be selected is from 1 to about 20 percent with 10 percent being preferred, although other effective concentrations can be selected. The aldehyde can be selected, for example, from the group consisting of formaldehyde, acetaldehyde and butylaldehyde and the like. The ratio of the nitroaryl cyclobutene dione to aldehyde can be from about 2 to about 100 with 2 to 20 being preferred, although other effective concentrations can be selected. The pressure of the hydrogen selected for the reductive alkylation process is usually, but is not limited to, about 10 to 100 psi with 20 to 80 psi being preferred.

The 1-p-nitroaryl-2-hydroxycyclobutene-3,4-dione selected in the reductive alkylation process can be prepared by the known [2+2] cycloaddition process involving a tetraalkoxy olefin and a p-nitroaryl ketene generated in situ by the reaction of a p-nitroarylacetyl chloride or other halide and a base. Thus, for example, p-nitrophenylacetyl chloride can be reacted with tetraethoxyethylene in diethyl ether solvent in the presence of triethylamine. The ratio of acid chloride to tetraethoxyethylene is, for example, from about 1 to 10 with 1 to 4 being preferred. The amount of triethylamine used will vary, however, usually an amount equivalent to the amount of the acid chloride is selected. Also, the above reaction mixture is stirred at room temperature (25° to 30° C.) until the reaction is completed. The [2+2] cycloadduct mixture can be hydrolyzed directly by refluxing in an aqueous hydrochloric acid solution. The hydrolyzed product is then purified by conventional techniques such as recrystallization, and the like. This results in 1-p-nitrophenyl-2-hydroxycyclobutene-3,4-dione, which can be reductive alkylated to form 1-p-dimethylaminophenyl-2-hydroxycyclobutene-3,4-dione, which can then be reacted with an N,N-dialkylaniline as described herein.

Illustrative specific examples of unsymmetrical and symmetrical fluorinated squaraines obtained with the process of the present invention include those as illustrated herein such as

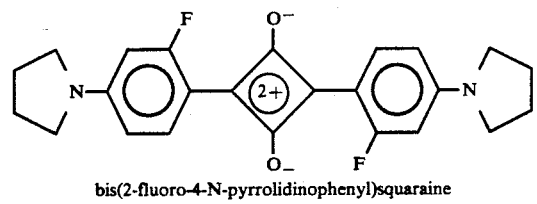

bis(2-fluoro-4-N-pyrrolidinophenyl)squaraine

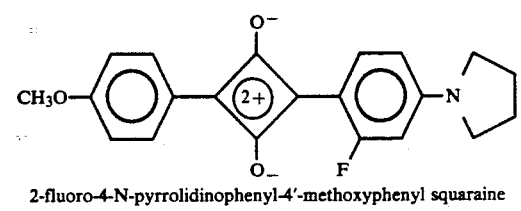

2-fluoro-4-N-pyrrolidinophenyl-4′-methoxyphenyl squaraine

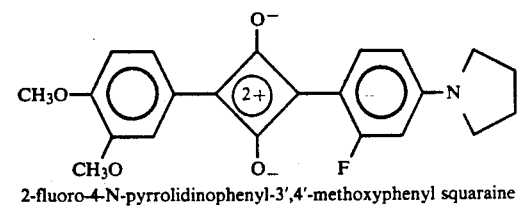

2-fluoro-4-N-pyrrolidinophenyl-3′,4′-methoxyphenyl squaraine

-continued

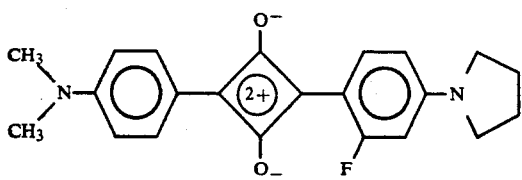

2-fluoro-4-N-pyrrolidinophenyl-4'-dimethylaminophenyl squaraine.

The fluorinated squaraine compounds of the present invention can be selected for various photoconductive imaging members. One member is comprised of a supporting substrate, a hole transport layer, and as a photoconductive layer situated between the supporting substrate and the hole transport layer the fluorinated squaraines of the present invention. In another embodiment, there is envisioned a layered photoresponsive device comprised of a supporting substrate, a photoconductive layer comprised of the fluorinated squaraine compound of the present invention, and situated between the supporting substrate and the photoconductive layer, a hole transport layer. In one specific illustrative embodiment, the photoresponsive device can be comprised of (1) a supporting substrate, (2) a hole blocking layer, (3) an optional adhesive interface layer, (4) fluorinated squaraine of the present invention photogenerating layer, and (5) a hole transport layer. A specific photoresponsive device of the present invention can be comprised of a conductive supporting substrate, a hole blocking metal oxide layer in contact therewith, an adhesive layer, a photoconductive layer comprised of the fluorinated squaraine illustrated herein as photogenerating pigments overcoated on the optional adhesive layer, and as a top layer, a hole transport layer comprised of certain diamines dispersed in a resinous matrix. The photoconductive layer composition when in contact with the hole transport layer is capable of allowing holes generated by the photogenerating layer to be transported. Examples of aryl amine hole transport molecules that may be selected for the photoconductor devices are illustrated in U.S. Pat. No. 4,265,990, the disclosure of which is totally incorporated herein by reference.

The photoresponsive devices or imaging members described herein can be incorporated into various imaging systems such as those conventionally known as xerographic imaging processes. Additionally, the imaging members of the present invention can be selected for imaging and printing systems with visible light and/or infrared light. In this embodiment, the photoresponsive devices may be negatively charged, exposed to light in a wavelength of from about 400 to about 1,000 nanometers, and preferably from about 450 to about 850, either sequentially or simultaneously, followed by developing the resulting image with toner and transferring to paper. The above sequence may be repeated many times.

BRIEF DESCRIPTION OF THE DRAWINGS

For a better understanding of the features of the present invention, the following detailed description of various preferred embodiments is provided wherein
FIGS. 1 to 6 represent process reaction schemes.

DESCRIPTION OF THE PREFERRED EMBODIMENTS

Preferred embodiments of the invention will now be illustrated, it being noted that substantially equivalent imaging members are also embraced within the scope of the present invention.

Figure 1:
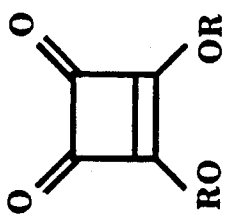
Figure 1:
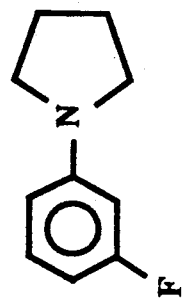
Figure 1:
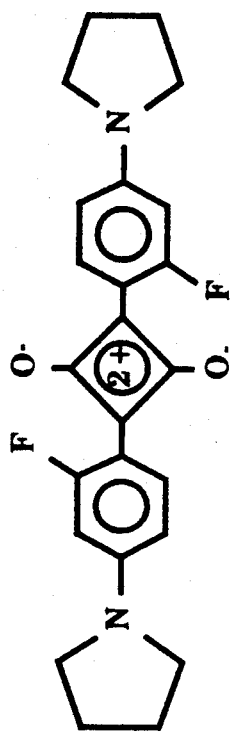
Figure 2:
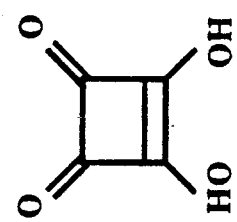
Figure 2:
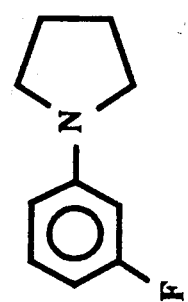
Figure 2:
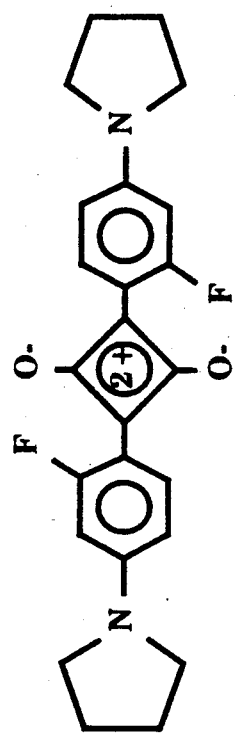
Figure 5:
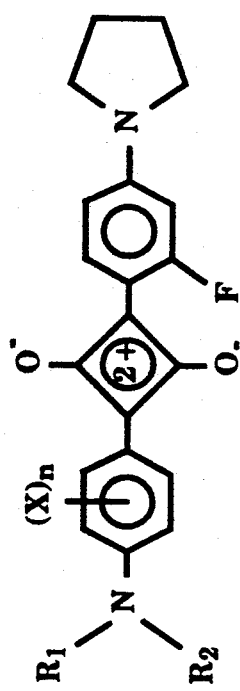
Figure 5:
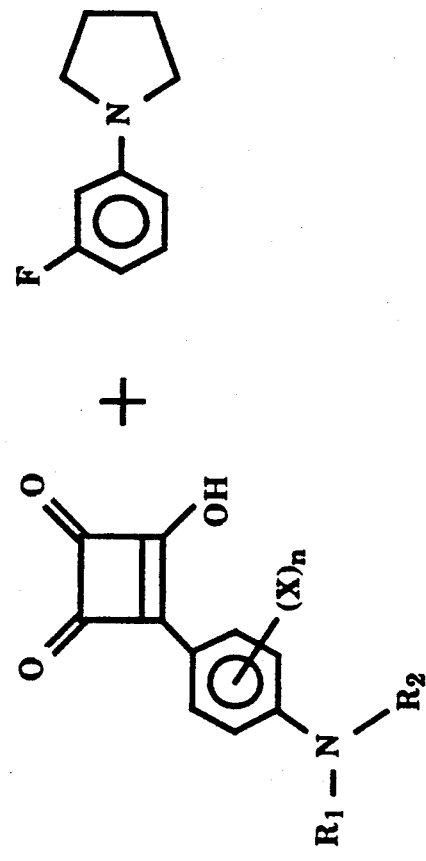
Figure 6:
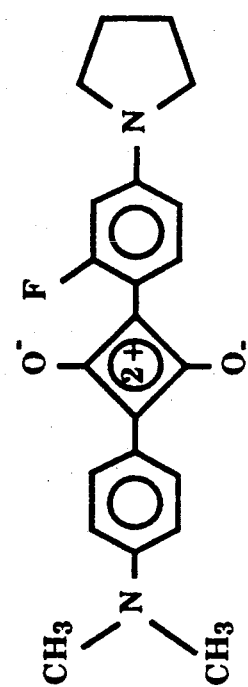
Figure 6:
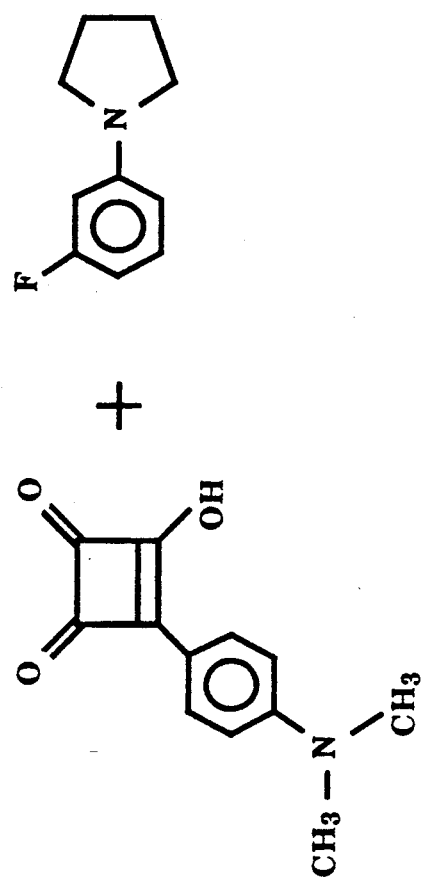
Figure 7:
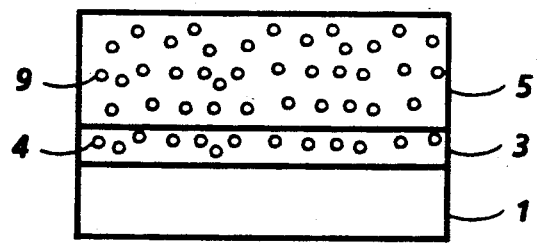
FIGS. 7, 8 and 9 are partially schematic views of the photoconductive imaging members of the present invention.

FIG. 7 illustrates a photoconductive imaging member of the present invention comprising a supporting substrate 1, a photogenerating layer 3 comprising the fluorinated squaraines illustrated herein optionally dispersed in a resinous binder composition 4, and a charge carrier hole transport layer 5, which comprises a hole transporting molecule dispersed in an inactive resinous binder composition 9.

Figure 8:
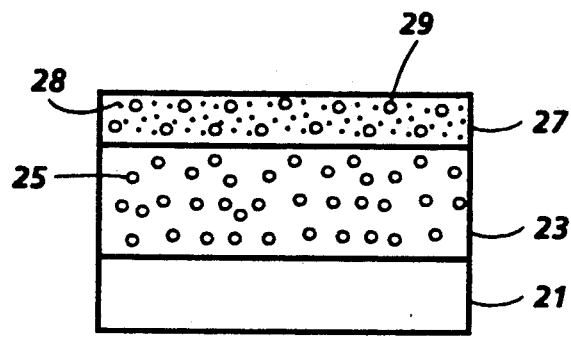

FIG. 8 illustrates the same member as that shown in FIG. 7 with the exception that the hole transport layer is situated between the supporting substrate and the photogenerating layer. More specifically, this figure illustrates a photoconductive imaging member comprising a supporting substrate 21, a hole transport layer 23 comprising an aryl amine charge or hole transport composition dispersed in an inactive resinous binder composition 25, and a photogenerating layer 27 comprising the fluorinated squaraine 28 of the formulas as illustrated herein optionally dispersed in a resinous binder composition 29.

Figure 9:
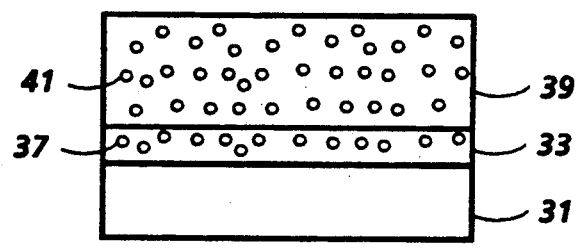

FIG. 9 illustrates a photoconductive imaging member of the present invention comprising a supporting substrate 31, a photogenerating layer 33 comprising one of the fluorinated squaraines represented by the following formulas:

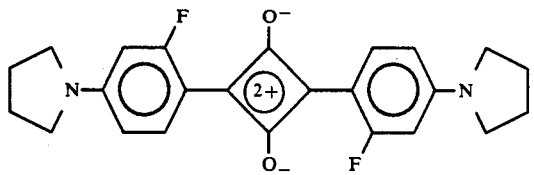

bis(2-fluoro-4-N-pyrrolidinophenyl)squaraine

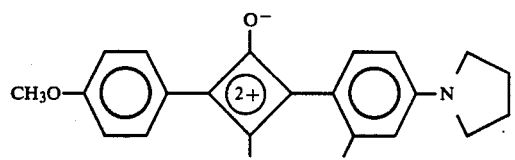

2-fluoro-4-N-pyrrolidinophenyl-4'-methoxyphenyl squaraine

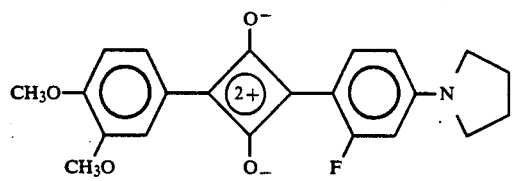

2-fluoro-4-N-pyrrolidinophenyl-3',4'-methoxyphenyl squaraine, or

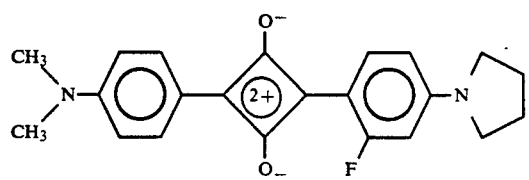

-continued 2-fluoro-4-N-pyrrolidinophenyl-4'-dimethylaminophenyl squaraine optionally dispersed in a resinous binder composition 37, and a charge carrier hole transport layer 39, which comprises a hole transporting molecule dispersed in an inactive resinous binder composition 41.

The supporting substrate of the imaging members may comprise an insulating material such as an inorganic or organic polymeric material, including Mylar ®, a commercially available polymer; a layer of an organic or inorganic material having a semiconductive surface layer such as indium tin oxide or aluminum arranged thereon; or a conductive material such as aluminum, titanium, chromium, nickel, brass, or the like. The substrate may be flexible, seamless, or rigid and may have a number of different configurations, such as a plate, a cylindrical drum, a scroll, an endless flexible belt, and the like. Preferably, the substrate is in the form of an endless flexible belt. In some situations, it may be desirable to coat an anticurl layer, such as polycarbonate materials commercially available as Makrolon ®, on the back of the substrate, particularly when the substrate is an organic polymeric material.

The thickness of the substrate layer depends on a number of factors, including economic considerations, the componets of the other layers, and the like. Thus, this layer may be of substantial thickness, for example over 100 mils, or of minimal thickness provided that there are no adverse effects on the system. In a preferred embodiment, the thickness of this layer is from about 3 mils to about 15 mils.

Generally, the fluorinated squaraine photogenerating layer has a thickness of from about 0.05 micron to about 10 microns or more, and preferably has a thickness of from about 0.1 micron to about 4 microns. The thickness of this layer, however, is dependent primarily upon the photogenerating weight loading, which may vary from about 5 to 100 percent, the components of the other layers, and the like. Generally, it is desirable to provide this layer in a thickness sufficient to absorb a substantial amount, for example about 90 percent or more, of the incident radiation which is directed upon it in the imagewise or printing exposure step. The maximum thickness of this layer is dependent primarily upon factors such as mechanical considerations, such as the specific squaraine compound selected, the thicknesses of the other layers, and whether a flexible photoconductive imaging member is desired. Optionally, resin binders for the photogeneration layer include polyvinyl carbazole, and the like as illustrated herein.

The hole transport layer can be comprised of various components providing, for example, that they effectively transport charges (holes) such as an aryl amine compound dispersed in a resinous binder. Preferred hole transport layers are comprised of aryl amine compounds of the formula:

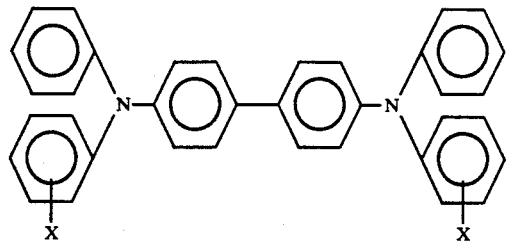

wherein X is selected from the group consisting of alkyl and halogen. Preferably, X is selected from the group consisting of methyl and chloride in either the ortho, meta, or para positions. Suitable inactive binder materials for the hole transport layer include known highly insulating resins, which generally have a resistivity of at least $10^{12}$ ohm-cm to prevent undue dark decay. Compounds corresponding to the above formula include N,N'-diphenyl-N,N'-bis(alkylphenyl)-[1,1'-biphenyl]-4,4'-diamine, wherein alkyl is selected from the group consisting of methyl, such as 2-methyl, 3-methyl and 4-methyl, ethyl, propyl, butyl, hexyl, and the like. With halo substitution, the amine is N,N'-diphenyl-N,N'-bis(-halo phenyl)-[1,1'-biphenyl]-4,4'-diamine, wherein halo is 2-chloro, 3-chloro or 4-chloro. Other electrically active small molecules that can be dispersed in the electrically inactive resin to form a layer which will transport holes include bis(4-diethylamino-2-methylphenyl)-phenyl methane, 4',4"-bis(diethylamino)-2',2"-dimethyltriphenyl methane, bis-4-(diethylaminophenyl)phenyl methane, and 4,4'-bis(diethylamino)-2,2'-dimethyltriphenyl methane. Generally, the hole transport layer has a thickness of from about 5 to about 75 microns, and preferably of from about 10 to about 40 microns.

Examples of highly insulating and transparent resinous components or inactive binder resinous material for the transport layer include materials such as those described in U.S. Pat. No. 3,121,006, the disclosure of which is totally incorporated herein by reference. Specific examples of suitable organic resinous materials include polycarbonates, arcylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight of from about 20,000 to about 100,000 with a molecular weight in the range of from about 50,000 to about 100,000 being particularly preferred. The materials most preferred as electrically inactive resinous materials are poly(4,4'-dipropylidine-diphenyline carbonate) with a weight average molecular weight of from about 35,000 to about 40,000 available as Lexan 145 from General Electric Company; poly(4,4'-isopropylidine-diphenyline carbonate) with a weight average molecular weight of from about 40,000 to about 45,000 available as Lexan 141 from General Electric Company; a polycarbonate resin having a weight average molecular weight of from about 50,000 to about 100,000 available as Makrolon from Farbenfabricken Bayer AG; and a polycarbonate having a weight average molecular weight of from about 20,000 to about 50,000 available as Merlon from Mobay Chemical Company. Generally, the resinous binder contains from about 10 to about 75 percent by weight of the active material corresponding to the foregoing formula, and preferably from about 35 percent to about 50 percent of this material. Examples of binder material for the squaraine photogenerating layer are poly(vinyl acetal) polycarbonates as mentioned herein, polyesters, polyvinyl carbazole, and the like. Typical effective amounts of binder can be selected including, for example, from about 5 to about 95, and preferably from about 10 to about 70 weight percent, in embodiments of the present invention, and providing that squaraine enables photogeneration.

The photoconductive imaging member may optionally contain a hole blocking layer situated between the supporting substrate and the photogenerating layer. This layer may comprise metal oxides, such as aluminum oxide and the like, or materials such as silanes. The primary purpose of this layer is to prevent hole injection from the substrate during and after charging. Typically, this layer is of a thickness of less than 50 Angstroms, although it may be as thick as 500 Angstroms in some instances.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone and the like. Typically, this layer is of a thickness of less than about 0.6 micron.

Imaging members of the present invention exhibit excellent xerographic properties in embodiments thereof. For example, values for dark development potential ($V_{ddp}$) range from about $-400$ to about $-975$. Preferred ranges for dark development potential for the imaging members of the present invention are usually about $-400$ to $-500$ volts with $-800$ volts being especially preferred. High dark development potentials permit high contrast potentials, which result in images of high quality with essentially no background development.

The imaging members of the present invention in embodiments thereof also exhibit low dark decay values of about $-50$ volts per second or less. Low dark decay values are of importance for developing high quality images since dark decay measures the amount of charge that disappears after charging of the photoreceptor, and a large difference in charge between exposed and unexposed areas of the photoreceptor results in images with high contrast. Acceptable values for dark decay vary depending on the design of the imaging apparatus in which the imaging members are contained. This dark decay may be as high as $-100$ volts per second with $-50$ volts, and $-10$ to $-20$ volts per second being preferred.

Residual potential values ($V_R$) for the imaging members of the present invention in embodiments thereof are excellent, ranging from about $-5$ volts to about $-50$ volts. Residual potential is a measure of the amount of charge remaining on the imaging member after erasure by exposure to light and prior to imaging. Residual potentials of $-5$ to $-10$ are considered exceptional.

Photosensitivity values ($E_{0.5ddp}$ at 600 nanometers) for the imaging members of the present invention in embodiments thereof are acceptable and, in some instances excellent, and range from about 4 to about 25 ergs per square centimeter. Acceptable photosensitivity values vary depending on the design of the imaging apparatus in which the imaging members are contained; thus in some instances, values as high as 40 or 50 are acceptable, and values of about 5 are preferred.

The present invention also encompasses a method of generating images with the photoconductive imaging members disclosed herein. The method comprises the steps of generating an electrostatic image on a photoconductive imaging member of the present invention, subsequently developing the electrostatic image with known developer compositions comprised of resin particles, pigment particles, additives, including charge control agents and carrier particles, reference U.S. Pat. Nos. 4,558,108; 4,560,535; 3,590,000; 4,264,672; 3,900,588; and 3,849,182, the disclosures of each of these patents being totally incorporated herein by reference, transferring the developed electrostatic image to a suitable substrate, and permanently affixing the transferred image to the substrate. Development of the image may be achieved by a number of methods, such as cascade, touchdown, powder cloud, magnetic brush, and the like. Transfer of the developed image to a substrate may be by any method, including those wherein a corotron or a biased roll is selected. The fixing step may be performed by means of any suitable method, such as flash fusing, heat fusing, pressure fusing, vapor fusing, and the like.

The imaging members of the present invention can be prepared by a number of different known processes such as those illustrated in the U.S. Pat. No. 4,886,722, the disclosure of which is totally incorporated herein by reference. In one process embodiment, the squaraine photogenerator is coated onto a supporting substrate with a Bird applicator, for example, followed by the solution coating of the charge transport layer, and thereafter drying in, for example, an oven.

The following examples are being supplied to further define various species of the present invention, it being noted that these examples are intended to illustrate and not limit the scope of the present invention. Parts and percentages are by weight unless otherwise indicated.

EXAMPLE I

Sodium carbonate (45 grams, 0.43 mole) and iodide (0.86 gram) was suspended in 650 milliliters of 1-butanol in a 1 liter 3-necked flask. The mixture was stirred and brought to reflux. 1,4-Dibromobutane (93.5 grams, 0.43 mole) and m-fluoroaniline (48 grams, 0.43 moles) were introduced separately into the reaction flask. The addition rates of both reactants were adjusted in such a fashion that they were introduced evenly (in terms of molarity) and slowly in about 6 hours. After the addition was completed, the reaction mixture was cooled to room temperature. Any sodium carbonate formed was removed by filtration. After evaporation by heating of all the butanol solvent, a clear brown liquid, 47.7 grams, was obtained. The brown liquid was then stirred with 50 milliliters of acetic acid anhydride overnight (16 hours). The mixture was transferred to a 2 liter beaker and was chilled by an ice water bath. Concentrated hydrochloric acid was added carefully to the ice cold acetic acid anhydride solution in the 2 liter beaker. The acidic solution was extracted with ether (3×300 milliliters) to remove any neutral or acidic impurities. After the extraction, the resulting solution was transferred back to a 2 liter beaker and was chilled by an ice water bath. It was then strongly basified by NaOH pellets. The alkaline solution was extracted with ether (3×250 milliliters). The ether extracts were combined and were dried over $MgSO_4$. After gravity filtration and solvent evaporation, a brown liquid resulted. The product, which was subsequently identified as N-pyrrolidino-3- fluoroaniline, was isolated and purified by vacuum distillation, yield 39.1 grams (55 percent). There resulted a product with a b.p.: 122° to 125° C. at about 8.3 millimeters Hg.

$^1$H NMR (CDCl$_3$): δ1.98 to 2.03 (m, 4H), 3.26 (t,J=6.6 Hz, 4H), 6.21 to 6.26 (m, 1H), 6.30 to 6.36 (m, 2H) and 7.13 (q,J=8 Hz, 1H); and MS (m/z): 165 (M+).

Analysis Calculated for C$_{10}$H$_{12}$NF: C 72.70, H 7.32, N 8.48, F 11.50, Found: C 72.50, H 7.30, N 8.52, F 11.36.

EXAMPLE II 1-p-Methoxyphenyl-2-hydroxycyclobutene-3,4-dione was synthesized according to the procedure reported by Bellus *J. Am. Chem. Soc.*, 100, 8026 (1978), the disclosure of which is totally incorporated herein by reference. A slight modification to the aforesaid process was accomplished as follows:

Tetraethoxyethylene, which was freshly synthesized using the procedure of Bellus et al. *Helv. Chim. Acta.*, 63, 1130 (1980), (59.6 grams, 0.29 mole), triethylamine (63.7 grams), and n-hexane (1,350 milliliters) was discharged in a 3 liter three-neck flask which was equipped with a mechanical stirrer and a nitrogen inlet. 4-Methoxyphenylacetyl chloride (113.1 grams, 0.61 mole) was added slowly through a pressure equalizing funnel in a two hour period. A white precipitate of triethylamine hydrochloride was formed during the addition. After the addition was completed, the resulting mixture was stirred at room temperature for about 4 hours. Subsequently, the resulting mixture was warmed by a water bath (about 60° C.) for 0.5 hour through a 1.5 liter medium sintered glass funnel. The solid obtained was washed with warm n-hexane (3×1,300 milliliters), and the n-hexane solutions were combined. After removing the solvent under reduced pressure, a light yellow liquid, 96.4 grams, resulted. This yellow liquid was then dissolved in about 3,500 milliliters of ether, 1,000 grams of basic alumina (from Fisher Scientific, activity III) was added, and the resulting slurry was stirred for 6 hours. The slurry was filtered and the alumina was washed thoroughly with ether. After evaporating the hexane solvent, 73 grams of yellow liquid was obtained. This yellow liquid was hydrolyzed with 400 milliliters, 18 percent of hydrochloric acid at reflux for 4 hours. The hydrochloric acid was evaporated under reduced pressure. The residue, a brown gummy solid, was then digested with n-hexane on a steambath resulting in a brown solid product. This crude product was then recrystallized from a mixture of toluene and acetone to yield 35 grams of the above desired dione product (57 percent), m.p.: 221° to 223° C.; IR(KBr): 1,723 and 1,794 cm$^{-1}$ (C=O); $^1$H NMR (acetone-d$_6$) δ3.91 (s, 3H, OCH$_3$), 7.17 (d, 2H,J=9.4 Hz), and 8.07 (d, 2H,J=9.4 Hz); MS (m/z):204 (M+).

EXAMPLE III 1-3',4'-Dimethoxyphenyl-2-hydroxycyclobutene-3,4-dione, 42 percent yield, was prepared according to the procedure as described in Example II with the exception that the basic alumina treatment was omitted. There resulted the above dione product with a m.p.: 238° to 239° C.; IR(KBr): 1,713 and 1,790 cm$^{-1}$; $^1$H NMR (acetone-d$_6$) δ3.91 (s, 3H, OCH$_3$), 3.94 (s, 3H, OCH$_3$), 7.17 (d, 1H,J=7.9 Hz), 7.64 (d, 1H,J=2Hz), and 7.75 (ABq, 1H, J$_A$=7.9 Hz, J$_B$=2Hz); and MS (m/z): 234 (M+).

Analysis Calculated for C$_{12}$H$_{10}$O$_5$: C 61.54, H 4.30, Found: C 61.30, H 4.41.

EXAMPLE IV

Para (p)-nitrophenylaceticacid (60.6 grams) and phorphorous pentachloride (74.4 grams) were charged into a 1 liter neck reaction flask. The aforementioned two solid compounds were mixed gently with a glass rod and an exothermic reaction was observed which was accompanied by the formation of phorphorous oxychloride. When the exotherm subsided, the formed mixture was brought to reflux at an oil-bath temperature of about 120° C. for about 2 hours. The resulting mixture was then cooled to about 60° C. and phorphorous oxychloride was removed under reduced pressure. The crude product was then recrystallized from n-heptane (about 1.5 liters) to yield pure p-nitrophenylacetyl chloride (white solid), 53.6 grams, 83 percent; m.p. 47.5° to 49° C.

EXAMPLE V 1-p-Nitrophenyl-2-hydroxycyclobutene-3,4-dione was synthesized by a [2+2] cycloaddition reaction similar to that reported by Bellus *J. Am. Chem. Soc.*, 100, 8026 (1978), the disclosure of which is totally incorporated herein by reference.

Tetraethoxyethylene, which was freshly synthesized using the procedure of Bellus et al. *Helv. Chim. Acta.*, 63, 1130 (1980), (51.3 grams, 0.25 mole), the disclosure of which is totally incorporated herein by reference, triethylamine (54.8 grams), and diethyl ether solvent (1.6 liters) was charged into a 3 liter three-neck flask which was equipped with a mechanical stirrer and a nitrogen inlet. An ethereal solution containing 105.2 grams of the p-nitrophenylacetyl chloride of Example IV in 800 milliliters of ether was added into the tetraethoxyethylene solution slowly at room temperature in a two hour period. A light brown precipitate was formed during the addition. The resulting product mixture was maintained at 25° to 30° C. by a warm water bath for 4 more hours. The product resulting, which was soluble in diethyl ether, was isolated by filtration. The formed insoluble precipitate was then washed with another liter of ether. After solvent evaporation, 83.2 grams of yellow residue was obtained. The yellow residue was then hydrolyzed with 150 milliliters of 18 percent hydrochloric acid at reflux for 4.5 hours. Hydrochloric acid was evaporated under reduced pressure to yield 46.5 grams of crude product (a tan color gum). The crude product was then digested with boiling n-hexane and was recrystallized from a mixture of acetone and toluene. A light yellow solid, 1-p-nitrophenyl-2-hydroxycyclobutene-3,4-dione, was obtained, yield 28.1 grams, 51 percent; m.p. 162° to 163° C. (dec.); IR(KBr): 1,822, 1,790 and 1,724 cm$^{-1}$, (C=O); $^1$H NMR (DMSO-d$_6$) δ8.05 to 8.4 ppm (AB quartlet); and MS (m/z): 219 (M+).

Analysis Calculated for C$_{12}$H$_{10}$O$_5$: C 54.81, H 2.30, N 6.39, Found: C 54.91, H 2.86, N 6.57.

EXAMPLE VI

A solution containing 8.77 grams of the 1-p-nitrophenyl-2-hydroxycyclobutene-3,4-dione of Example V in 160 milliliters DMF (dimethylformamide) was placed in a 500 milliliter Parr bottle. Thereafter, 8.8 milliliters, 37 percent, of formaldehyde solution and 2.4 grams of catalyst (10 percent Palladium on carbon) were added. The Parr bottle was then placed on a Parr apparatus and the mixture was hydrogenated by hydrogen at a pressure of about 60 psi at about 50° C. for about 1.5 hours.

The catalyst was removed by filtration and the solvent was evaporated under reduced pressure. The resulting orange-brown residue was then digested with acetone. After vacuum drying, 7.02 grams, 80.8 percent, the orange solid, 1-p-dimethylaminophenyl-2-hydroxycyclobutene-3,4-dione, was obtained. m.p.>300° C. (dec.); IR(KBr): 1,695 and 1,748 cm$^{-1}$, (C=O); $^1$H NMR (DMSO-d$_6$) δ3.04, (s, 6H, NCH$_3$), 6.86 (d, 2H,J=9.6 Hz) and 7.87 (d, 2H,J=9.6 Hz; and MS (m/z): 217 (M+).

Analysis Calculated for $C_{12}H_{11}NO_3$: C 66.35, H 5.10, N 6.45, Found: C 64.61, H 5.17, N 6.95.

EXAMPLE VII

Squaric acid, 1.14 grams (10 millimoles) and 3.47 grams (21 millimoles) of N-pyrrolidino-3-fluoroaniline prepared in accordance with the process of Example I was heated to reflux in a mixture of toluene (40 milliliters) and 1-butanol (40 milliliters) at an oil bath temperature of about 130° C. Water was removed azeotropically by a Dean Stark trap. After 8 hours, the reaction mixture was cooled to room temperature. The product bis(2-fluoro-4-N-pyrrolindinophenyl) squaraine was collected by filtration. After washing the product with methanol and ether and vacuum drying, 1.72 grams (42 percent) of a light blue solid was obtained. m.p.=247° C. (dec.); IR(KBr): 1,598 cm$^{-1}$ (squaraine).

Analysis Calculated for $C_{24}H_{22}N_2O_2F_2$: C 70.58, H 5.43, N 6.86, F 9.30, Found: C 70.30, H 5.46, N 6.87, F 9.94.

EXAMPLE VIII 1-p-Methoxyphenyl-2-hydroxycyclobutene-3,4-dione (1.7 grams, 8.3 millimoles) and N-pyrrolidino-3-fluoroaniline (1.44 grams, 8.7 millimoles), which were prepared in accordance with the processes of Examples II and I, respectively, were reacted in 65 milliliters of 2-propanol at reflux under an N$_2$ atmosphere in the presence of 6.2 milliliters of tributyl orthoformate. After about two hours of refluxing, the reaction mixture was cooled to an ice cold temperature. The precipitated product 2-fluoro-4-N-pyrrolidinophenyl-4'-methoxy phenyl squaraine was isolated by filtration. After washing the product with cold, 500 milliliters, 2-propanol and ether and vacuum drying, 1.81 grams (62 percent) of a purple blue squaraine product was obtained. m.p.=216° C. (dec.); IR(KBr)=1,591 and 1,622 cm$^{-1}$.

Analysis Calculated for $C_{21}H_{18}NO_3F$: C 71.78, H 5.16, N 3.99, F 5.41, Found: C 72.09, H 5.27, N 4.00, F 4.84.

EXAMPLE IX

The process of Example VIII was repeated with the exception that 1-3',4'-dimethoxyphenyl-2-hydroxycyclobutene-3,4-dione, which was prepared in accordance with the process of Example III, was used in place of 1-p-methoxyphenyl-2-hydroxycyclobutene-3,4-dione to yield 72 percent of 2-fluoro-4-N-pyrrolidinophenyl-3',4'-dimethoxyphenyl squaraine. m.p.=210° C. (dec.); IR(KBr): 1,588 and 1,620 cm$^{-1}$ (squaraine).

Analysis Calculated for $C_{22}H_{20}NO_4F$: C 69.28, H 5.29, N 3.67, F 4.98, Found: C 69.12, H 5.36, N 3.76, F 4.76.

EXAMPLE X

2-Fluoro-4-N-pyrrolidinophenyl-4'-dimethylaminophenyl squaraine was prepared by reacting the 1-p-dimethylaminophenyl-2-hydroxycyclobutene-3,4-dione of Example VI with N-pyrrolidino-3-fluoroaniline of Example I in refluxing 2-propanol in the presence of tributyl orthoformate. N-pyrrolidino-3-fluoroaniline (0.76 gram, 4.6 millimoles), 45 milliliters of 2-propanol and 2 millimeters of tributyl orthoformate were charged into a 100 milliliter three-necked flask, which was equipped with a magnetic stir bar and a nitrogen inlet. The mixture was stirred and brought to reflux. A solution containing 1-(p-dimethylaminophenyl)-2-hydroxycyclobutene-3,4-dione (0.5 gram, 2.3 millimoles) in 8 milliliters of N,N-dimethylformamide was added slowly through a pressure equalizing funnel in a three hour period. After the addition was completed, the product mixture was kept at reflux for three more hours. The precipitated product was isolated by filtration. After washing with N,N-dimethylformamide, methanol and vacuum drying, 0.11 gram of a dark blue solid, which was subsequently identified as 2-fluoro-4-N-pyrrolidinophenyl-4'-dimethylaminophenyl squaraine was obtained in 13 percent yield. m.p.=227° C. (dec.); IR(KBr)=1,559 and 1,620 cm$^{-1}$ (squaraine).

Analysis Calculated for $C_{22}H_{21}N_2O_2F$: C 72.51, H 5.81, N 7.69, Found: C 71.79, H 5.64, N 7.50.

EXAMPLE XI

There was prepared a photoresponsive device containing as the photoconductive material the fluorinated squaraine as prepared in accordance with Example VII, and as a charge transport layer an aryl amine dispersed in a resinous binder. Specifically, there was prepared a photoresponsive device by providing a ball grained aluminum substrate of a thickness of 150 microns, followed by applying thereto with a multiple clearance film applicator in a wet thickness of 0.5 mil, a layer of N-methyl-3-aminopropyltrimethoxysilane, available from PCR Research Chemicals, Florida, in ethanol in a 1:20 volume ratio. This layer was then allowed to dry for 5 minutes at room temperature, followed by curing for 10 minutes at 110° C. in a forced air oven.

A photoconductive layer containing 30 percent by weight of bis(2-fluoro-4-N-pyrrolidinophenyl) squaraine and 70 percent by weight of Makrolon was then prepared as follows:

In a 2 ounce amber bottle, there was added 0.09 gram of the above squaraine, 0.2 gram of Makrolon (obtained from Larbensabricken Bayer A. G.), 85 grams of ⅛ inch stainless steel shots and 10 milliliters of methylene chloride. The above mixture was placed on a ball mill for 24 hours. The resulting slurry was then coated on the above silane layer using a 0.5 mil wet-gap Bird film applicator. The layer was then air dried for 5 minutes, and at 135° C. for 10 minutes in a forced air oven. The dry thickness of the squaraine layer was about 0.5 micron.

The above photoconductive layer was then overcoated with a charge transport layer, which was prepared as follows:

A transport layer composed of 50 percent by weight of Makrolon ®, a polycarbonate resin available from Larbensabricken Bayer A. G. was mixed with 50 percent by weight of the aryl armine N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to provide a layer with a dry thickness of 30 microns over the above squaraine photoconductive layer using a multiple clearance film applicator (5 mils wet gap thickness). The resulting device was then air dried at room temperature for 20 minutes, followed by drying in a forced air oven at 135° C. for 6 minutes.

The above photoreceptor device or photoconductive imaging member was then incorporated into a xerographic imaging test fixture and there resulted, subsequent to development of the latent images with toner particles containing a styrene n-butylmethacrylate resin, 88 weight percent, 8 weight percent of Regal 330 ® carbon black and 2 weight percent of the charge additive distearyl dimethyl ammonium methyl sulfate copies of excellent resolution and high quality.

EXAMPLE XII

There was prepared a photoresponsive device containing as the photoconductive material the fluorinated squaraine as prepared in accordance with Example VII, and as a charge transport layer an aryl amine dispersed in a resinous binder. Specifically, there was prepared a photoresponsive device by providing a ball grained aluminum substrate of a thickness of 150 microns, followed by applying thereto with a multiple clearance film applicator, in a wet thickness of 0.5 mil, a layer of N-methyl-3-aminopropyltrimethoxysilane, available from PCR Research Chemicals, Florida, in ethanol in a 1:20 volume ratio. This layer was then allowed to dry for 5 minutes at room temperature, followed by curing for 10 minutes at 110° C. in a forced air oven.

A photoconductive layer containing 80 percent by weight of bis(2-fluoro-4-N-pyrrolidinophenyl) squaraine and 20 percent by weight of poly(vinyl formal) was then prepared as follows:

In a 2 ounce amber bottle, there was added 0.21 gram of the above squaraine, 0.05 gram of poly(vinyl formal) obtained from Scientific Polymer Products, Inc., formal content 82 percent, acetate content 12 percent, hydroxy content 6 percent, 85 grams of ⅛ inch stainless steel shots and 10 milliliters of methylene chloride. The above mixture was placed on a ball mill for 24 hours. The resulting slurry was then coated on the silane layer using a 0.5 mil wet-gap Bird film applicator. The layer was then air dried for 5 minutes, and at 135° C. for 10 minutes in a forced air oven. The dry thickness of the squaraine layer was about 0.4 micron.

The above photoconductive layer was then overcoated with a charge transport layer, which was prepared as follows:

A transport layer composed of 50 percent by weight of Makrolon ®, a polycarbonate resin available from Larbensabricken Bayer A. G., was mixed with 50 percent by weight of the aryl armine N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to provide a layer with a dry thickness of 30 microns over the above squaraine photoconductive layer using a multiple clearance film applicator (5 mils wet gap thickness). The resulting device was then air dried at room temperature for 20 minutes, followed by drying in a forced air oven at 135° C. for 6 minutes.

The above photoreceptor device was then incorporated into a xerographic imaging test fixture and there resulted, subsequent to development of the formed latent images with the toner of Example XI, copies of excellent resolution and high quality.

EXAMPLE XIII

A photoconductive imaging member was prepared by providing a titanized Mylar substrate in a thickness of 3 mils and applying thereto a layer of silane as described in Example XI, and then a layer of 0.5 percent by weight of E. I. DuPont 49,000 adhesive in methylene chloride and 1,1,2-trichloroethane (4:1 volume ratio) with a Bird Applicator to a wet thickness of 0.5 mil. The layer was allowed to dry for one minute at room temperature, and 10 minutes at 100° C. in a forced air oven. The resulting layer has a dry thickness of 0.5 micron.

In a 2 ounce amber bottle, there was added 0.09 gram of bis(2-fluoro-4-N-pyrrolidinophenyl) squaraine, 0.2 gram of Makrolon, 85 grams of ⅛ inch stainless steel shots and 10 milliliters of methylene chloride. The above mixture was placed on a ball mill for 24 hours. The resulting slurry was then coated on the titanized Mylar substrate, and more specifically onto the 49000 adhesive layer using a 0.5 mil wet gap Bird Film Applicator. The layer was then air dried for 5 minutes and at 135° C. for 10 minutes in a forced air oven. The dry thickness of the squaraine layer was about 0.5 micron.

The above photoconductive layer was then overcoated with a charge transport layer, which was prepared as follows:

A transport layer composed of 50 percent by weight Makrolon ®, a polycarbonate resin available from Larbensabricken Bayer A. G., was mixed with 50 percent by weight N,N'-bis(3-methylphenyl)-1,1'-biphenyl-4,4'-diamine. This solution was mixed to 9 percent by weight in methylene chloride. All of these components were placed in an amber bottle and dissolved. The mixture was coated on the above squaraine photogenerating layer to provide a layer with a dry thickness of 30 microns, which coating was accomplished with a multiple clearance film applicator, 5 mils wet gap thickness. The resulting device was then air dried at room temperature for 20 minutes, followed by drying in a forced air oven at 135° C. for 6 minutes.

The above photoreceptor device was then incorporated into a xerographic imaging test fixture wherein latent images were generated on the photoreceptor. There resulted, subsequent to development of the images with toner particles containing a styrene n-butylmethacrylate resin, 88 percent, 10 percent of carbon black, and 2 weight percent of cetyl pyridinium chloride, and fixing by heat, images of excellent resolution and high quality with substantially no background deposits.

Photoresponsive devices can be prepared by repeating the procedure of Examples XI, XII and XIII with the exception that there was selected as the squaraine photoconductive composition 2-fluoro-4-N-pyrrolidinophenyl-4'-methoxyphenyl squaraine, 2-fluoro-4-N-pyrrolidinophenyl-3',4'-dimethoxyphenyl squaraine, or 2-fluoro-4-N-pyrrolidinophenyl-4'-dimethylaminophenyl squaraine.

The above members can then be tested for photosensitivity in the visible infrared region of the spectrum by negatively charging the devices with a corona to $-800$ volts, followed by simultaneously exposing each member to monochromic light from a tungsten lamp in the wavelength region of about 400 to about 900 nanometers. The photoresponsive devices will have excellent response, that is the devices discharged from $-800$ volts to about $-100$ volts at 10 ergs/cm$^2$ in the wavelength region of from about 400 to about 900 nanometers indicating both visible and infrared photosensitivity for these members.

Other modifications of the present invention will occur to those skilled in the art subsequent to a review of the present application. These modifications, and equivalents thereof are intended to be included within the scope of this invention.

What is claimed is:
1. The fluorinated squaraines

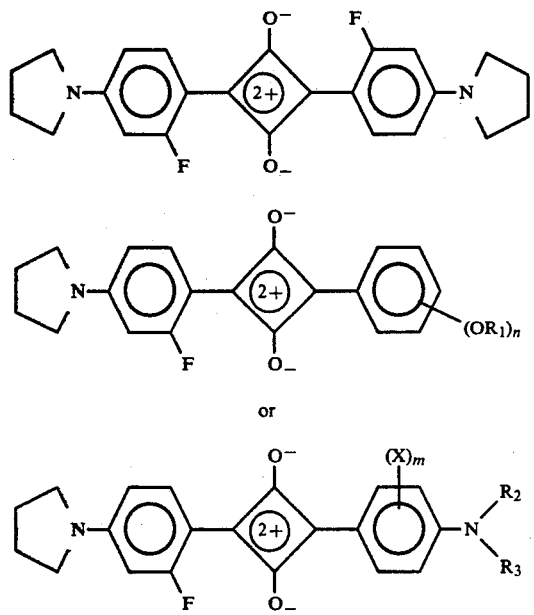

wherein $R_1$, $R_2$ and $R_3$ are independently selected from alkyl or aryl; X is hydrogen, hydroxy, alkyl, alkoxy or halogen; n is a number of 1 to about 3; and m is a number of from 0 to 2.

2. A squaraine in accordance with claim 1 wherein $R_1$ and $R_2$ are alkyl groups of from 1 to about 6 carbon atoms.

3. A photoconductive imaging member comprised of a supporting substrate, a photogenerating layer comprised of the squaraine A, B, or C of claim 1, and a hole transport layer.

4. A photoconductive imaging member in accordance with claim 3 wherein the photogenerating layer is situated between the supporting substrate and the hole transport layer.

5. A photoconductive imaging member in accordance with claim 3 wherein the hole transport layer is situated between the supporting substrate and the photogenerating layer.

6. A photoconductive imaging member in accordance with claim 3 wherein the photoconductive imaging member includes a metal oxide hole blocking layer situated between the supporting substrate and the photogenerating layer.

7. A photoconductive imaging member in accordance with claim 6 wherein the metal oxide is aluminum oxide.

8. A photoconductive imaging member in accordance with claim 6 wherein the metal oxide hole blocking layer has a thickness of less than about 500 Angstroms.

9. A photoconductive imaging member in accordance with claim 3 wherein the photoconductive imaging member contains an adhesive interface layer situated between the supporting substrate and the metal oxide hole blocking layer.

10. A photoconductive imaging member in accordance with claim 9 wherein the adhesive interface layer comprises a polymeric material selected from the group consisting of polyester, polyvinylbutyral, and polyvinyl pyrrolidone.

11. A photoconductive imaging member in accordance with claim 9 wherein the adhesive interface layer has a thickness of less than about 0.6 micron.

12. A photoconductive imaging member in accordance with claim 3 wherein the supporting substrate is a metal.

13. A photoconductive imaging member in accordance with claim 12 wherein the metal is aluminum or titanium.

14. A photoconductive imaging member in accordance with claim 3 wherein the supporting substrate is an organic polymeric composition.

15. A photoconductive imaging member in accordance with claim 3 wherein the supporting substrate has a thickness of from about 3 to about 100 mils.

16. A photoconductive imaging member in accordance with claim 3 wherein the supporting substrate has a thickness of from about 3 to about 10 mils.

17. A photoconductive imaging member in accordance with claim 3 wherein the squaraine layer has a thickness of from about 0.05 to about 10 microns.

18. A photoconductive imaging member in accordance with claim 3 wherein the squaraine layer has a thickness of from about 0.1 to about 3 microns.

19. A photoconductive imaging member in accordance with claim 3 wherein the hole transport layer has a thickness of from about 5 to about 50 microns.

20. A photoconductive imaging member in accordance with claim 3 wherein the squaraine compound is dispersed in a resinous binder in an amount of from about 5 percent by weight to about 95 percent by weight.

21. A photoconductive imaging member in accordance with claim 20 wherein the resinous binder is a polyester, polyvinyl butyral, a polycarbonate, polyvinyl carbazole or polyvinyl formal.

22. A photoconductive imaging member in accordance with claim 3 wherein the hole transport layer comprises an aryl amine compound.

23. A photoconductive imaging member in accordance with claim 22 wherein the aryl amine comprises molecules of the formula:

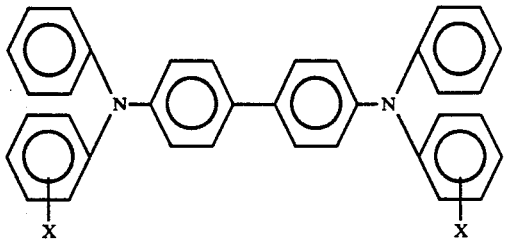

dispersed in a highly insulating and transparent organic resinous binder wherein X is selected from the group consisting of alkyl and halogen.

24. A photoconductive imaging member in accordance with claim 23 wherein X is selected from the group consisting of ortho (CH$_3$), meta (CH$_3$), para (CH$_3$), ortho (Cl), meta (Cl), and para (Cl).

25. A photoconductive imaging member in accordance with claim 23 wherein the resinous binder is a polyester, a polyvinyl butyral, a polycarbonate, or a polyvinyl formal.

26. A photoconductive imaging member in accordance with claim 3 wherein the imaging member exhibits a dark development potential of from about −500 to about −1,000 volts.

27. A photoconductive imaging member in accordance with claim 3 wherein the imaging member exhibits a dark decay of from about −10 to about −100 volts per second.

28. A photoconductive imaging member in accordance with claim 3 wherein the imaging member exhibits a residual potential of from about 1 to about 50 volts.

29. A photoconductive imaging member in accordance with claim 3 wherein the imaging member exhibits an E ½ photosensitivity of from about 3 to about 30 ergs/cm$^2$ at 600 nanometers.

30. A method of imaging which comprises the steps of:
   (a) generating an electrostatic image on the photoconductive imaging member of claim 3;
   (b) subsequently developing the electrostatic image;
   (c) transferring the developed electrostatic image to a suitable substrate; and
   (d) permanently affixing the transferred image to the substrate.

31. A method of imaging in accordance with claim 30 wherein the electrostatic image is developed by cascade, touchdown, powder cloud, or magnetic brush methods.

32. A method of imaging in accordance with claim 30 wherein the developed electrostatic image is transferred to a substrate by means of a corotron or a biased roll.

33. A method of imaging in accordance with claim 30 wherein the substrate is paper.

34. A method of imaging in accordance with claim 30 wherein the substrate is a transparency.

35. A fluorinated squaraine in accordance with claim 1 wherein alkyl contains from 1 to about 25 carbon atoms.

36. A fluorinated squaraine in accordance with claim 1 wherein aryl contains from 6 to about 24 carbon atoms.

37. A fluorinated squaraine in accordance with claim 1 wherein alkoxy contains from 1 to about 25 carbons atoms.

38. A fluorinated squaraine in accordance with claim 1 wherein n is the number 1, 2 or 3.

39. A fluorinated squaraine in accordance with claim 1 wherein m is the number 0, 1 or 2.

40. A photoconductive imaging member comprised of a photogenerating layer comprised of the squaraine A, B, or C of claim 1, and a hole transport layer.

41. A photoconductive imaging member comprised of the squaraine compound of claim 1, and a hole transport layer.

42. A photoconductive imaging member comprised of a supporting substrate, a photogenerating layer comprised of the squaraine A, B, or C of claim 1, and a charge transport layer.

43. Fluorinated squaraines selected from the group consisting of bis(2-fluoro-4-N-pyrrolidinophenyl)-squaraine; 2-fluoro-N-pyrrolidinophenyl-4'-methoxyphenyl squaraine; 2-fluoro-4-N-pyrrolidinophenyl-3',4'-methoxyphenyl squaraine; 2-fluoro-4-N-pyrrolidinophenyl-4'-dimethylaminophenyl squaraine; bis(2-fluoro-4-N-pyrrolidinophenyl) squaraine; 2-fluoro-4-N-pyrrolidinophenyl-4'-dimethylaminophenyl squaraine; 2-fluoro-4-N-pyrrolidinophenyl-2'-hydroxy-4'-dimethylaminophenyl squaraine; 2-fluoro-4-N-pyrrolidinophenyl-2'-methyl-4'-dimethylaminophenyl squaraine; 2-fluoro-4-N-pyrrolidinophenyl-4'-dimethylaminophenyl squaraine; 2-fluoro-4-N-pyrrolidinophenyl-2'-fluoro-4'-dimethylaminophenyl-squaraine; 2-fluoro-4-N-pyrrolidinophenyl-4'-methoxyphenyl squaraine; 2-fluoro-4-N-pyrrolidinophenyl-3',4'-dimethoxyphenyl squaraine; 2-fluoro-4-N-pyrrolidinophenyl-3',4',5'-trimethoxyphenyl squaraine; 2-fluoro-4-N-pyrrolidino-2'-methoxy-4'-dimethylaminophenyl squaraine; 2-fluoro-4-N-pyrrolidinophenyl-4'-methylbenzylaminophenyl squaraine; 2-fluoro-4-N-pyrrolidinophenyl-2'-chloro-4'-dimethylaminophenyl squaraine; 2-fluoro-4-N-pyrrolidinophenyl-9'-julolidinyl squaraine; 2-fluoro-4-N-pyrrolidinophenyl-8'-hydroxy-9'-julolidinyl squaraine; and 2-fluoro-4-N-pyrrolidinophenyl-8'-fluoro-9'-julolidinylsquaraine.

44. A photoconductive imaging member comprised of a supporting substrate, a hole transport layer, and a photogenerating layer comprised of at least one of the squaraines of claim 43.

45. A photoconductive imaging member comprised of a hole transport layer, and a photogenerating layer comprised of at least one of the squaraines of claim 43.

46. A process for the preparation of fluorinated squaraines which comprises the condensation of squaric acid and N-pyrrolidinofluoroaniline.

47. A process in accordance with claim 46 wherein the reaction is accomplished at a temperature of from about 60° C. to about 150° C.

48. A process in accordance with claim 46 wherein the pyrrolidone fluoroaniline is N-pyrrolidino-3-fluoroaniline.

49. A process for the preparation of fluorinated squaraines by the reaction schemes as illustrated in FIGS. 1,2,3,4,5 or 6.

50. A photoconductive imaging member in accordance with claim 49 wherein n is 2.

* * * * *